United States Patent [19]
Bakal et al.

[11] Patent Number: 6,156,332
[45] Date of Patent: Dec. 5, 2000

[54] METHOD AND COMPOSITION FOR MASKING MINERAL TASTE

[75] Inventors: Abraham I. Bakal, Parsippany; Margaret A. Snyder, Rockaway, both of N.J.

[73] Assignee: AMBI, Inc., Purchase, N.Y.

[21] Appl. No.: 09/320,449

[22] Filed: May 27, 1999

[51] Int. Cl.[7] .................................................. A61K 47/00
[52] U.S. Cl. .......................... 424/439; 424/400; 426/590; 426/648
[58] Field of Search ............................... 514/974; 424/439

[56] References Cited

U.S. PATENT DOCUMENTS

| | | | |
|---|---|---|---|
| 4,780,309 | 10/1988 | Geria et al. | 424/45 |
| 5,013,716 | 5/1991 | Cherukuri et al. | 514/23 |
| 5,059,416 | 10/1991 | Cherukuri et al. | 424/48 |
| 5,095,035 | 3/1992 | Eby, III | 514/494 |
| 5,106,632 | 4/1992 | Wong et al. | 426/3 |
| 5,124,144 | 6/1992 | Giorgetti et al. | 424/78.01 |
| 5,558,889 | 9/1996 | Rossi | 426/89 |
| 5,869,458 | 2/1999 | Waite et al. | 514/23 |
| 5,902,628 | 5/1999 | Shamil | 426/590 |
| 5,993,882 | 11/1999 | Hanger et al. | 426/548 |

OTHER PUBLICATIONS

"Behavioral Discrimination Between Quinine and KCI is dependent on Input from the Seventh Cranial Nerve: Implications for the Functional Roles of the gustatory Nerves in Rates", St. John SJ, J. Neurosci Jun. 1, 1998;18(11):4353–62.

"Specific Inhibitor for Bitter Taste: Inhibition of Frog Taste Nerve Responses and Human Taste Sensation to Bitter Stimulti", Y. Katsuragi, et al., Brain Res. Brain Res. Protoc. Aug. 1997:1(3):292–8.

*Primary Examiner*—Thurman K. Page
*Assistant Examiner*—P. E. McQueeney
*Attorney, Agent, or Firm*—Piper Marbury Rudnick & Wolfe, LLP; Steven B. Kelber

[57] ABSTRACT

The invention relates to methods and compositions for masking the taste of minerals in ingestible products. In particular, tannic acid glycyrrhizin and acesulfame potassium are added to compostions comprising minerals such as potassium, calcium, magnesium, iron, copper, chromium, zinc and mixtures in order to reduce or eliminate the unpleasant taste or aftertase associated with these minerals.

12 Claims, 11 Drawing Sheets

METHOD AND COMPOSITION FOR MASKING MINERAL TASTE

BACKGROUND OF THE INVENTION

Field of the Invention

The present invention relates to a method for masking unpleasant mineral tastes in ingestible products. The invention also relates to a composition containing minerals along with mineral taste-reducing agents.

DISCUSSION OF THE BACKGROUND

Products for ingestion, particularly beverages, which contain high concentrations of minerals, have a distinctive, unacceptable taste. The taste of these products is described as metallic, acrid or bitter and the corresponding products usually receive very low consumer acceptability scores.

The taste problems associated with minerals have been addressed with respect to salt substitutes, which are based on potassium salts (e.g., KCl). However in the case of salt substitutes, the issues are somewhat different than in the case of beverages and other ingestible products, because the objective in the case of salt substitutes is to impart to the KCl a salty taste, in addition to masking or decreasing the perception of the typical bitter taste or aftertaste associated with the potassium salt. In beverages and many other ingestible products, e.g. a nutrition bar, it is not necessary and usually undesirable to impart a salty taste to the finished product.

There are numerous medications which impact the balance of minerals whose concentration is essential to central body functions, including circulation and respiration, as well as metabolism. The balance of many of these electrolytes, including potassium, calcium and magnesium can be influenced or upset by these medications. Notable among them are diuretics. Patients receiving these medications are frequently required to supplement their diet with these minerals, typically in the form of a soluble powder, which is mixed with water to prepare a drink. These drinks, which are typically accompanied by an artificial citrus flavoring, are routinely characterized as bitter and unpleasant, such that the taste may become so obnoxious as to cause the patient to not consume the same when the medication is taken, which may jeopardize the patient's health.

Among the ingredients and compositions described in the literature for masking a KCl taste are such ingredients as amino acids, in particular L-lysine and glutamic acid, cream of tartar, and flavors including hydrolyzed yeast flavors. Other materials include choline tartrate, dextrose, lactose and the like.

While such ingredients are somewhat effective in reducing the aftertaste of salt substitutes, they are not effective in beverages and other ingestible products.

In view of the aforementioned deficiencies attendant with the prior art methods of masking the taste of minerals in beverages and other ingestible products, it is clear that there exists a need in the art for such methods and the corresponding compositions.

SUMMARY OF THE INVENTION

Accordingly, one object of this invention is to provide a novel method for reducing unpleasant taste and aftertaste caused by the presence of a mineral in an ingestible product, by adding to the ingestible product an amount of tannic acid, glycyrrhizin, or acesulfame potassium sufficient to reduce the taste or aftertaste caused by the mineral.

Another object of the invention is to provide a composition including a mineral which produces an unpleasant taste or aftertaste and an amount of tannic acid, glycyrrhizin, or acesulfame potassium sufficient to reduce the taste or aftertaste caused by the mineral.

According to a further object of the invention, the ingestible product is taken when medication is taken, to ensure replacement of electrolytes.

With the foregoing and other objects, advantages and features of the invention that will become hereinafter apparent, the nature of the invention may be more clearly understood by reference to the following detailed description of the preferred embodiments of the invention and to the appended claims.

DESCRIPTION OF THE PREFERRED EMBODIMENTS

Figure 1:
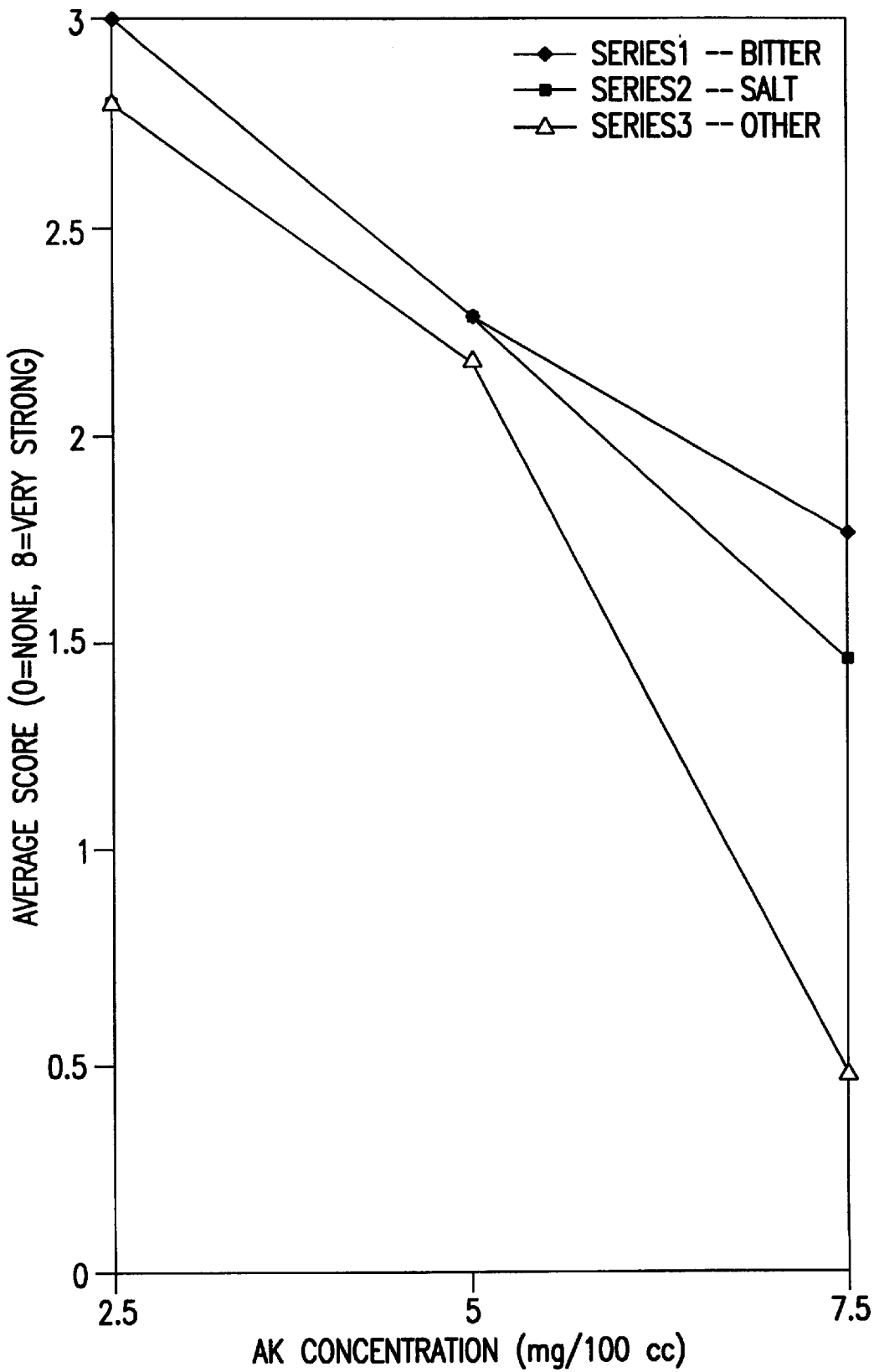
FIG. 1 is a graphic demonstration of the results of acesulfame potassium on the bitter and salt taste of KCl solutions.
Figure 2:
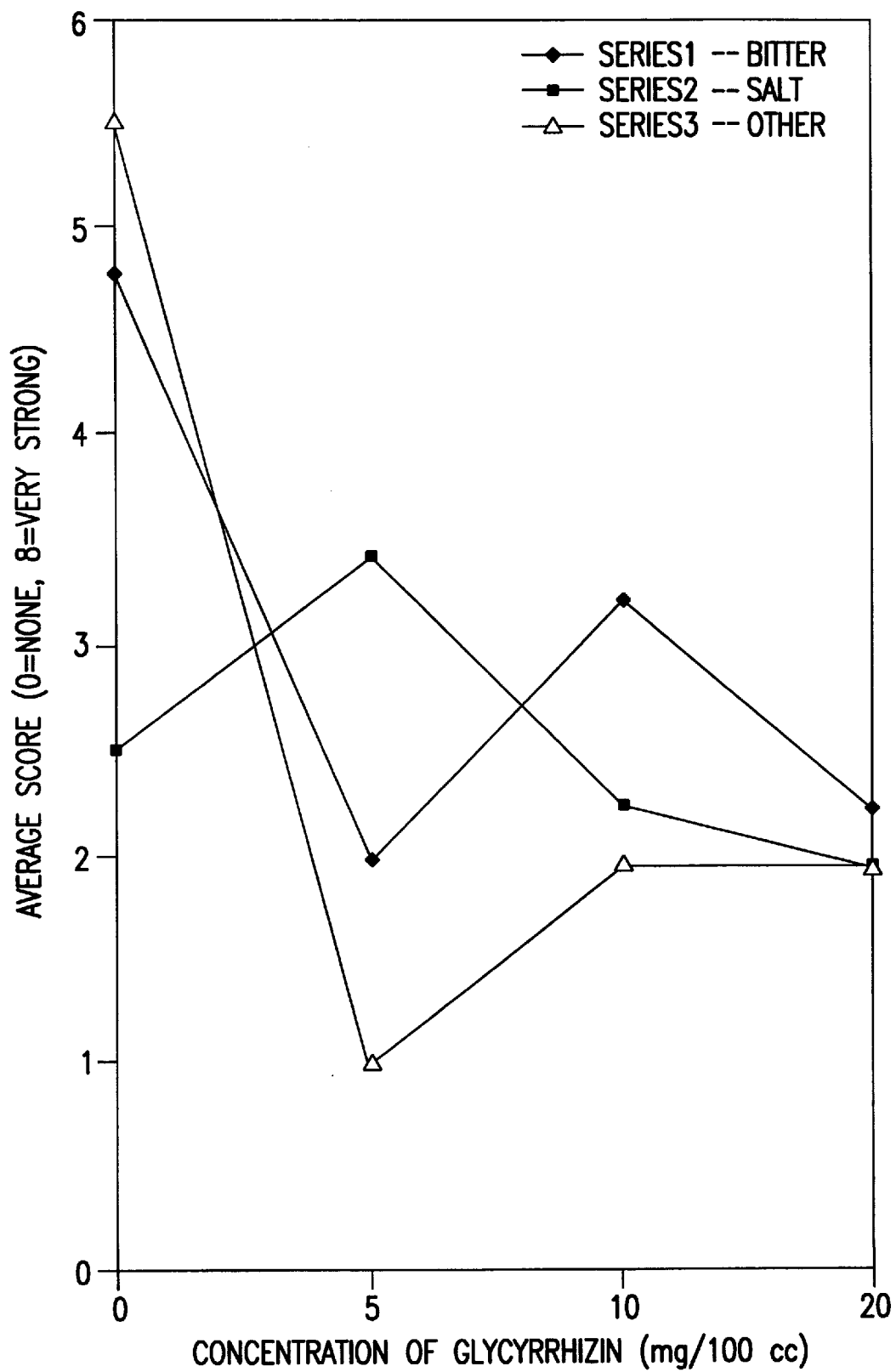
FIG. 2 is a graphic illustration of the effect of glycyrrhizin on the taste of KCl solutions.
Figure 3:
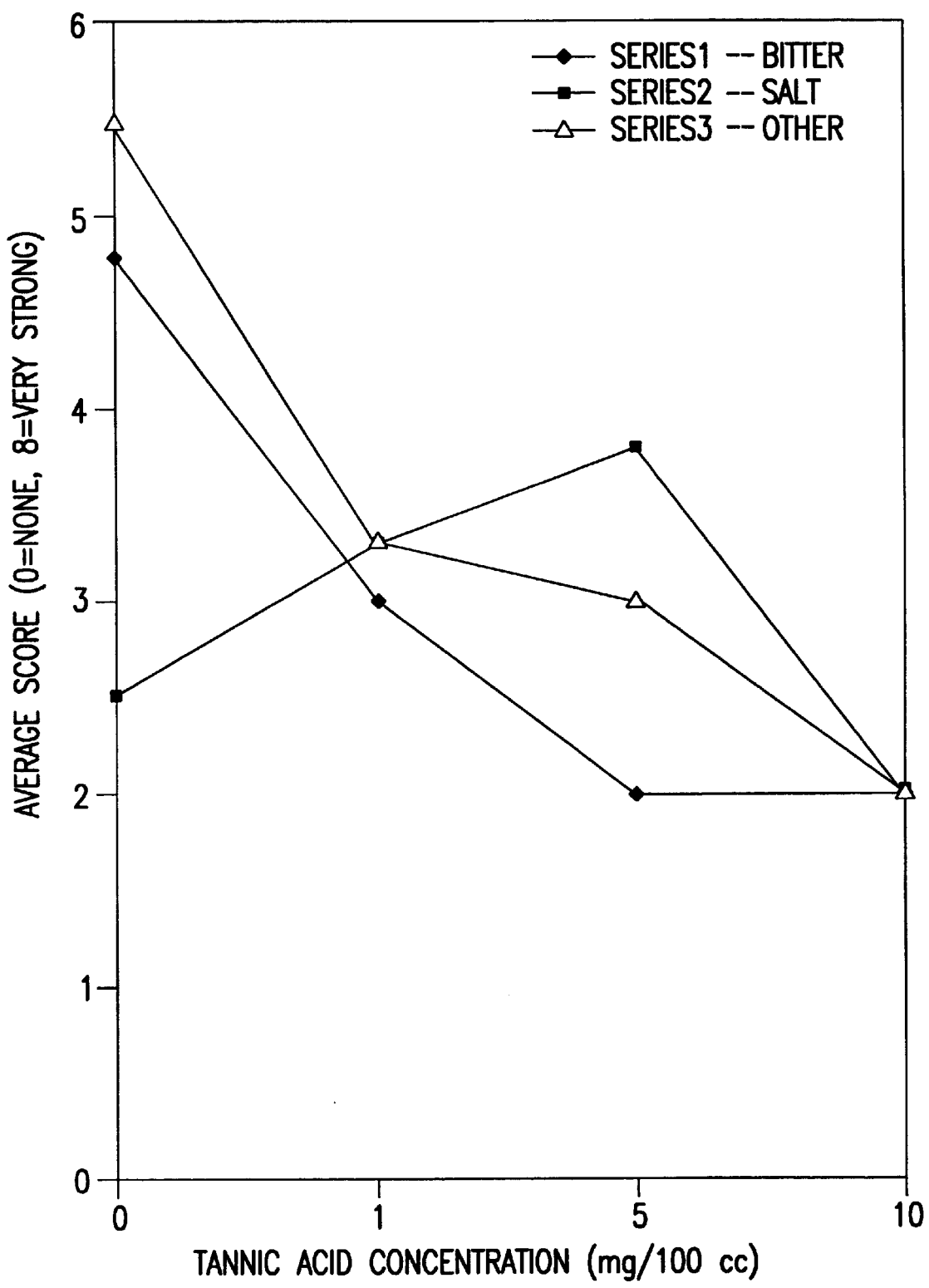
FIG. 3 is a graphic illustration of the effect of tannic acid on the taste of KCl solutions.
Figure 4:
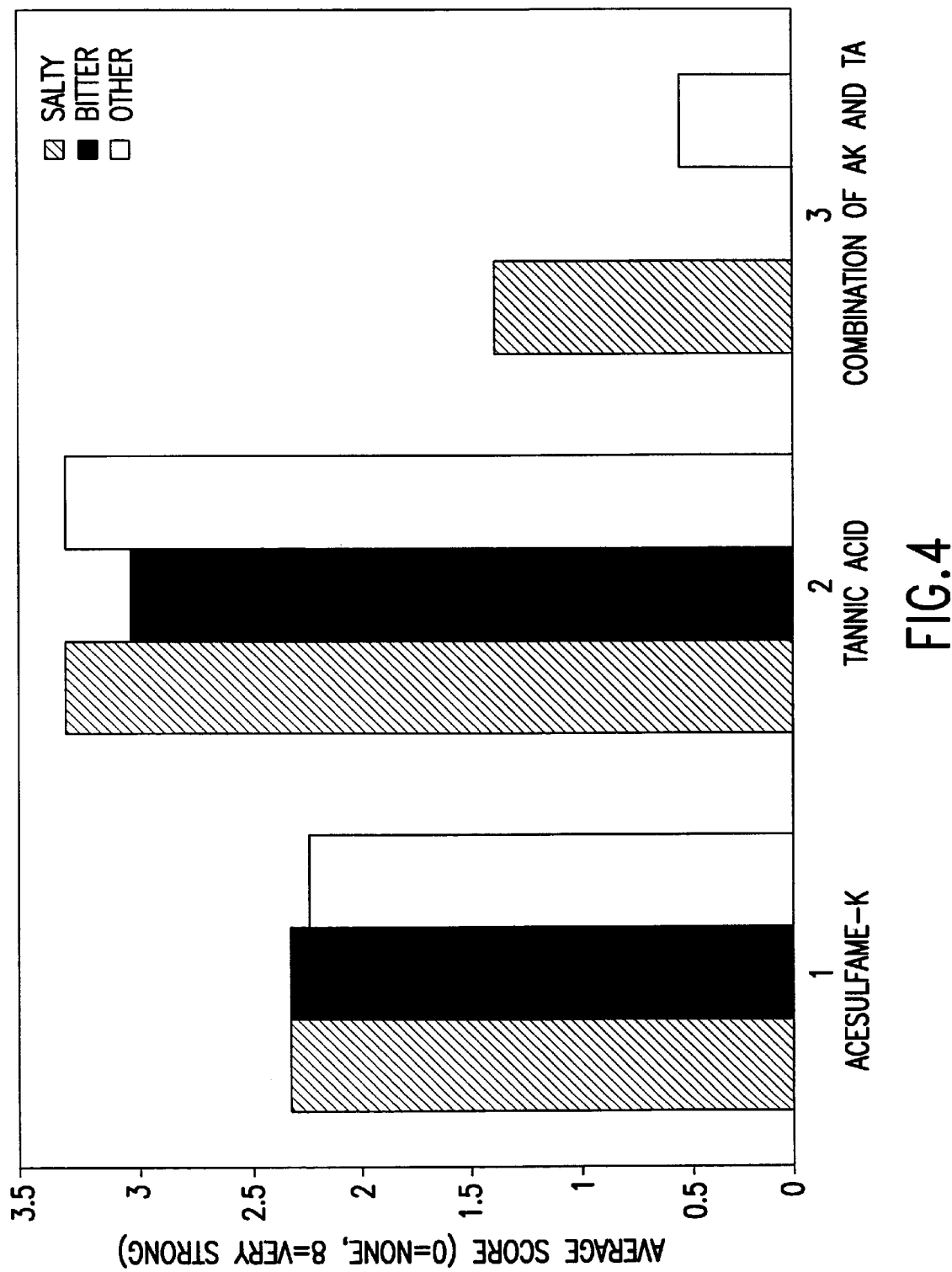
FIGS. 4–7 are bar graphs comparing the effect of acesulfame-K and tannic acid, as well as their combination, on the taste of KCl solutions, at various concentrations.
Figure 5:
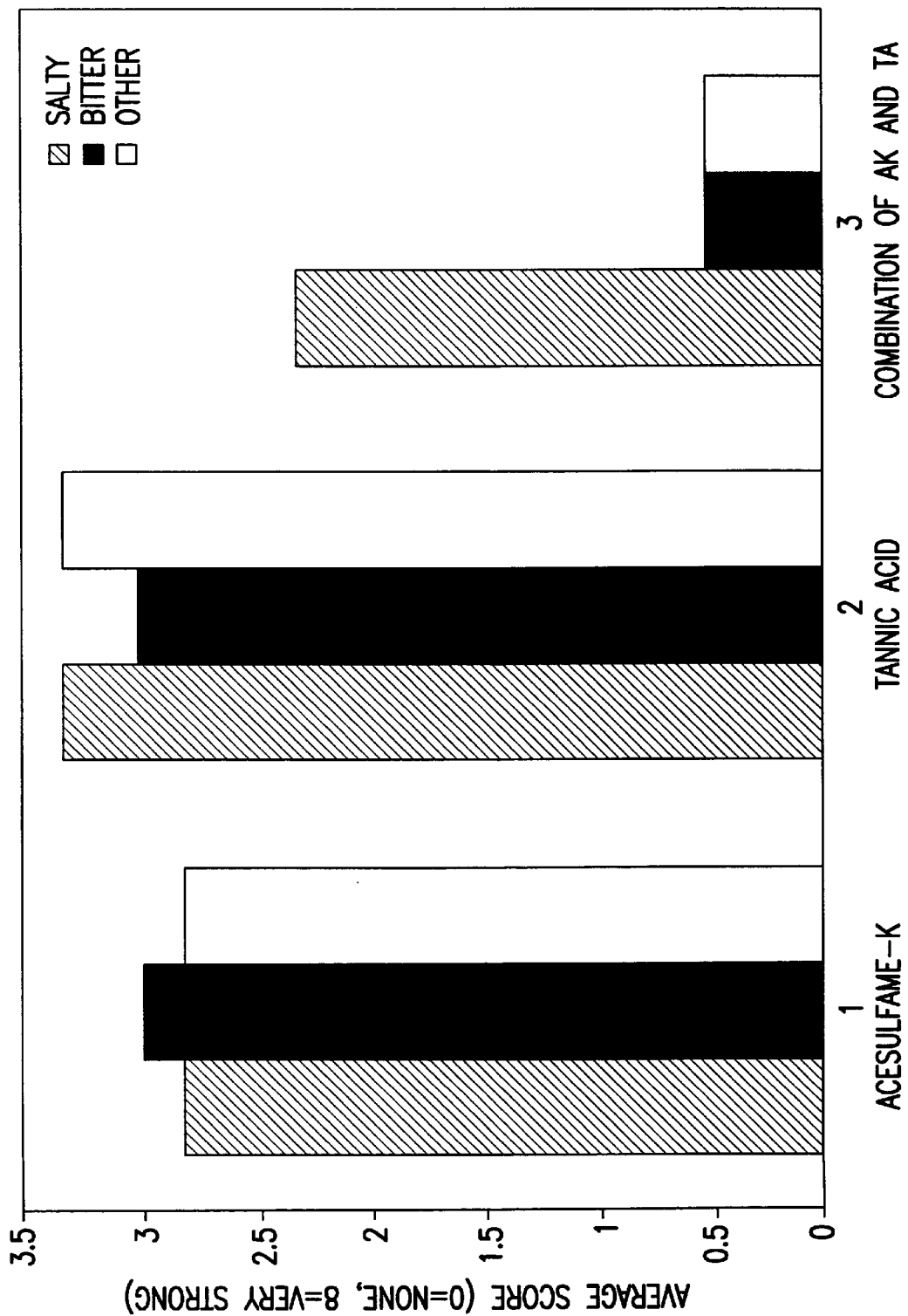
Figure 6:
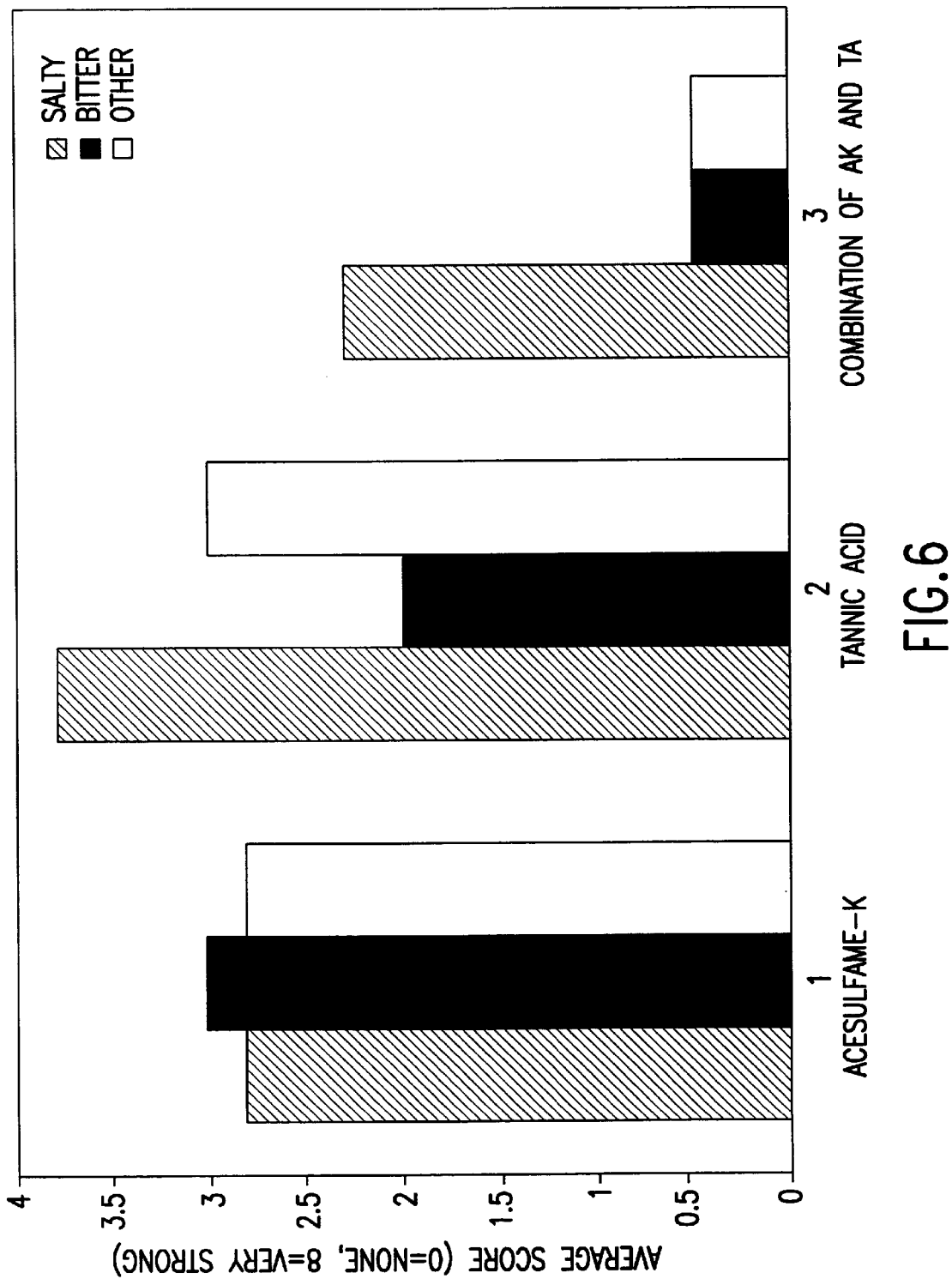
Figure 7:
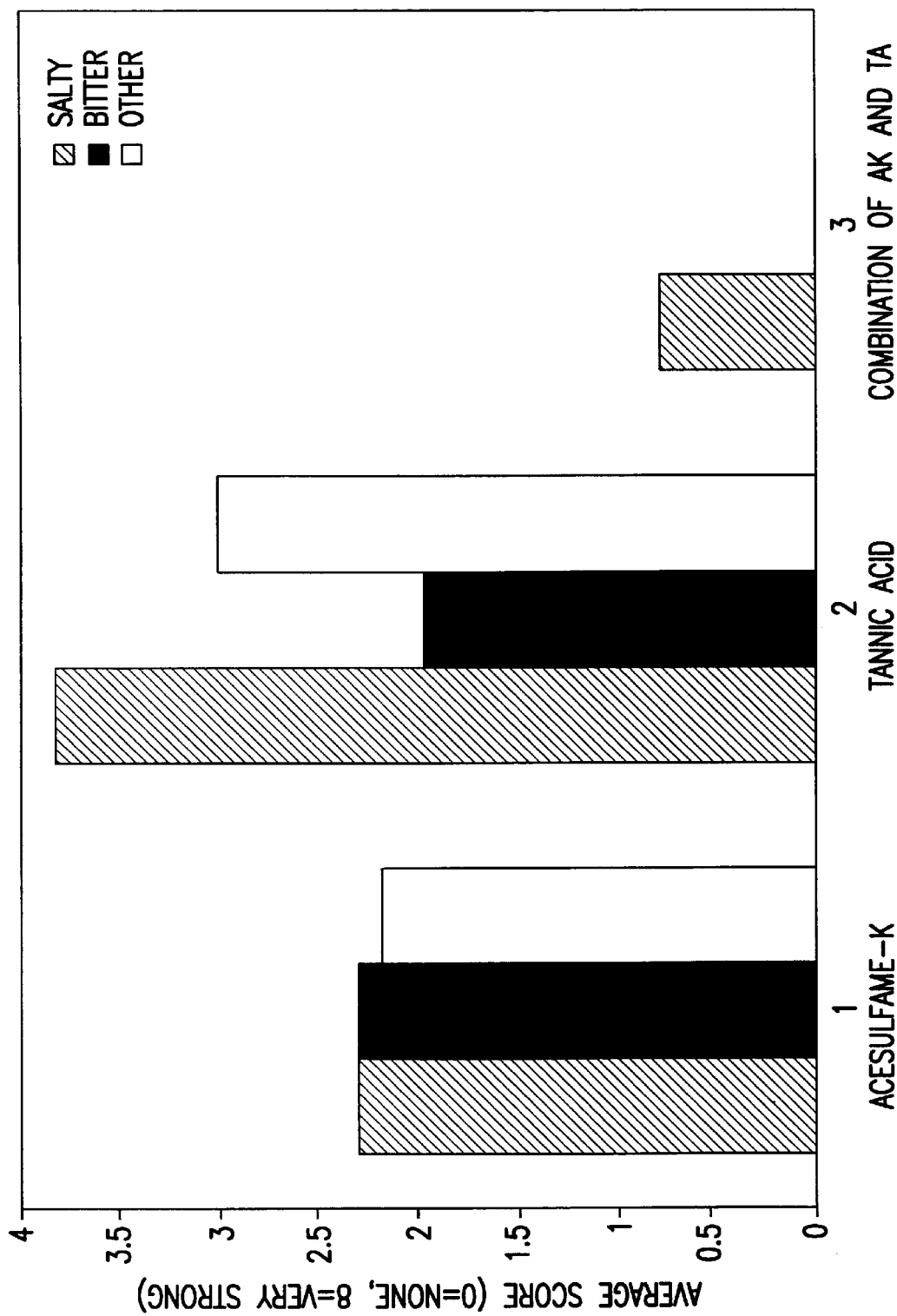
Figure 8:
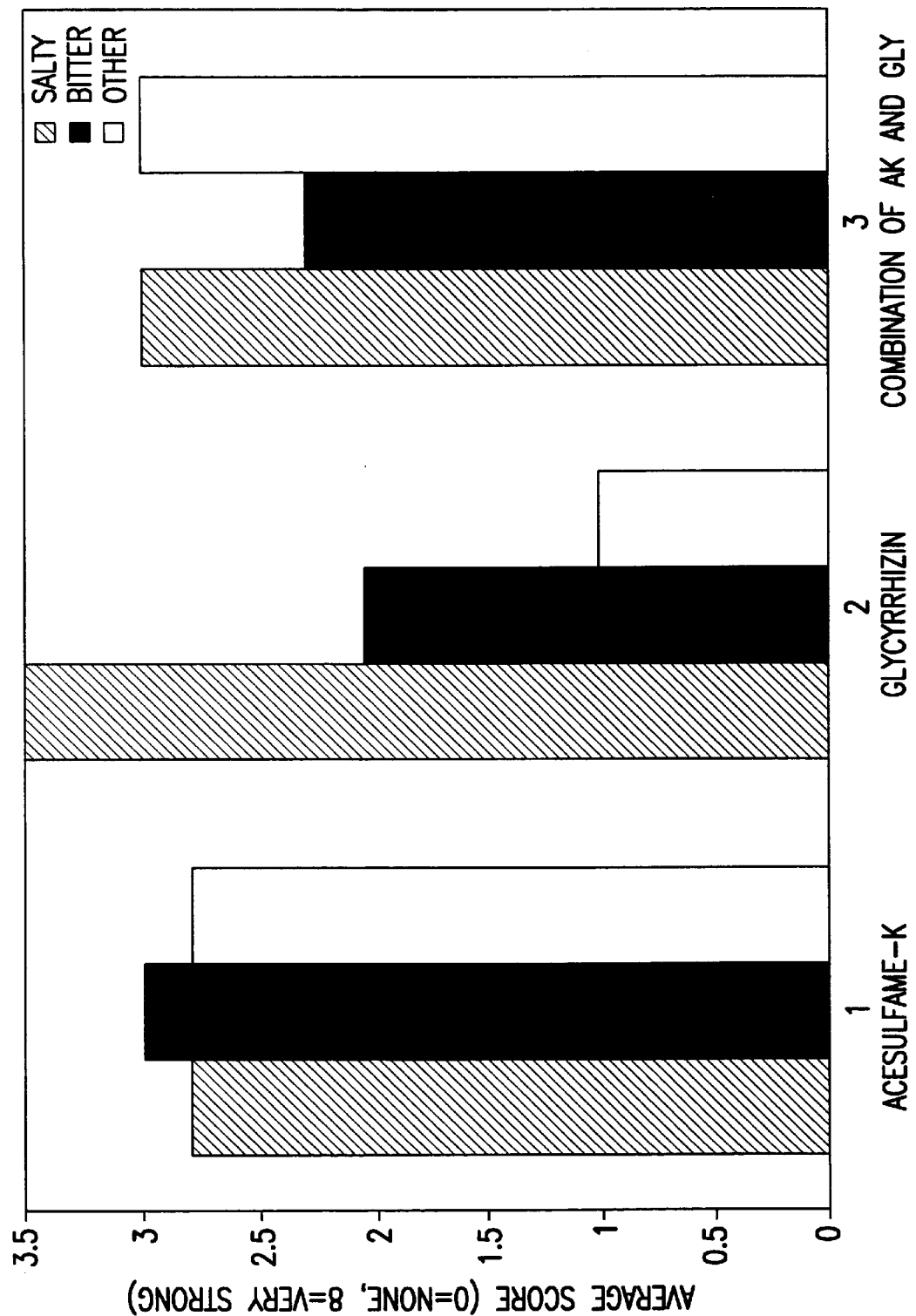
FIGS. 8–10 are bar graph illustrations of the effect of acesulfame-K and glycyrrhizin and their combination on the taste of KCl solutions.
Figure 9:
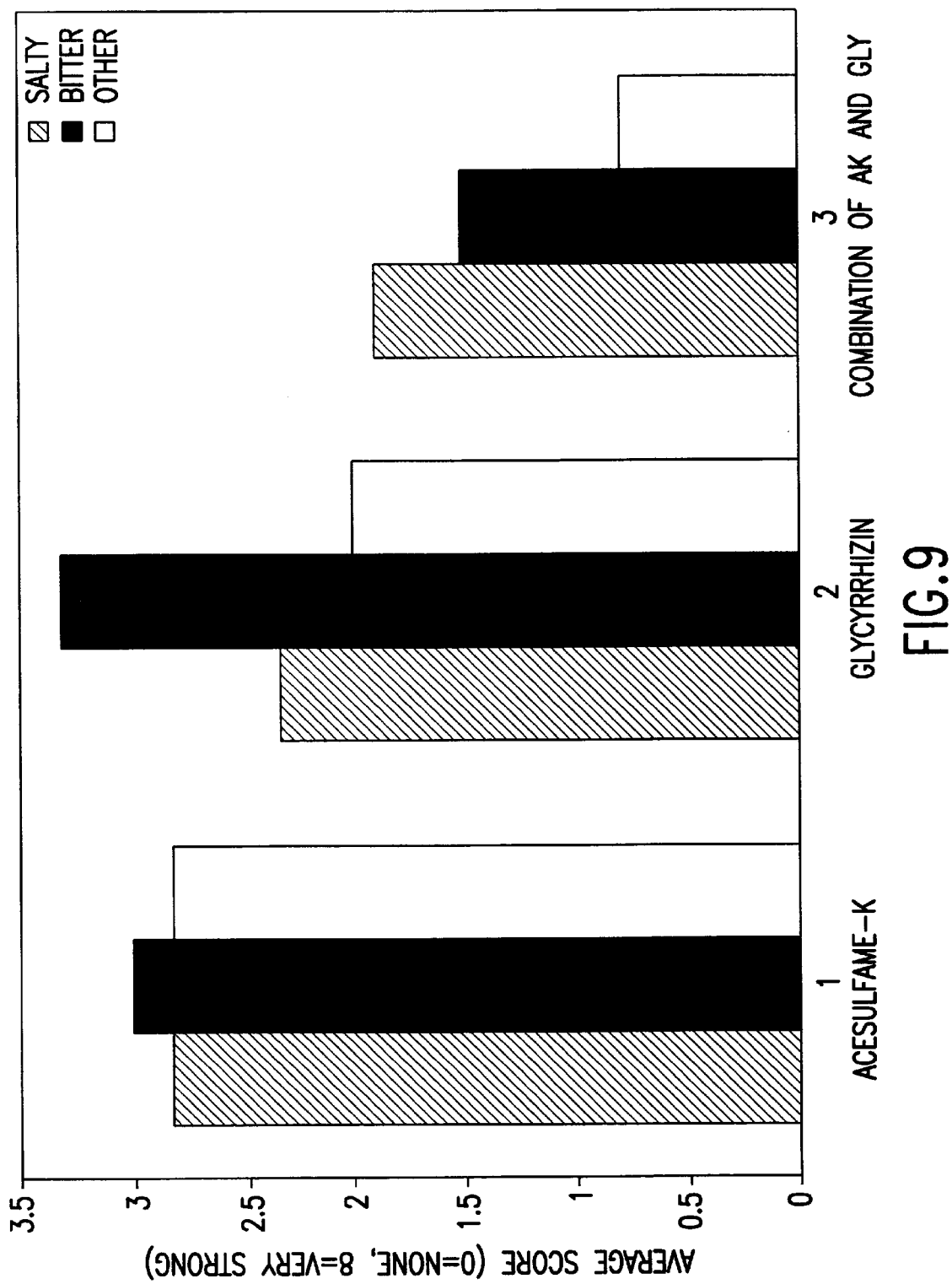
Figure 10:
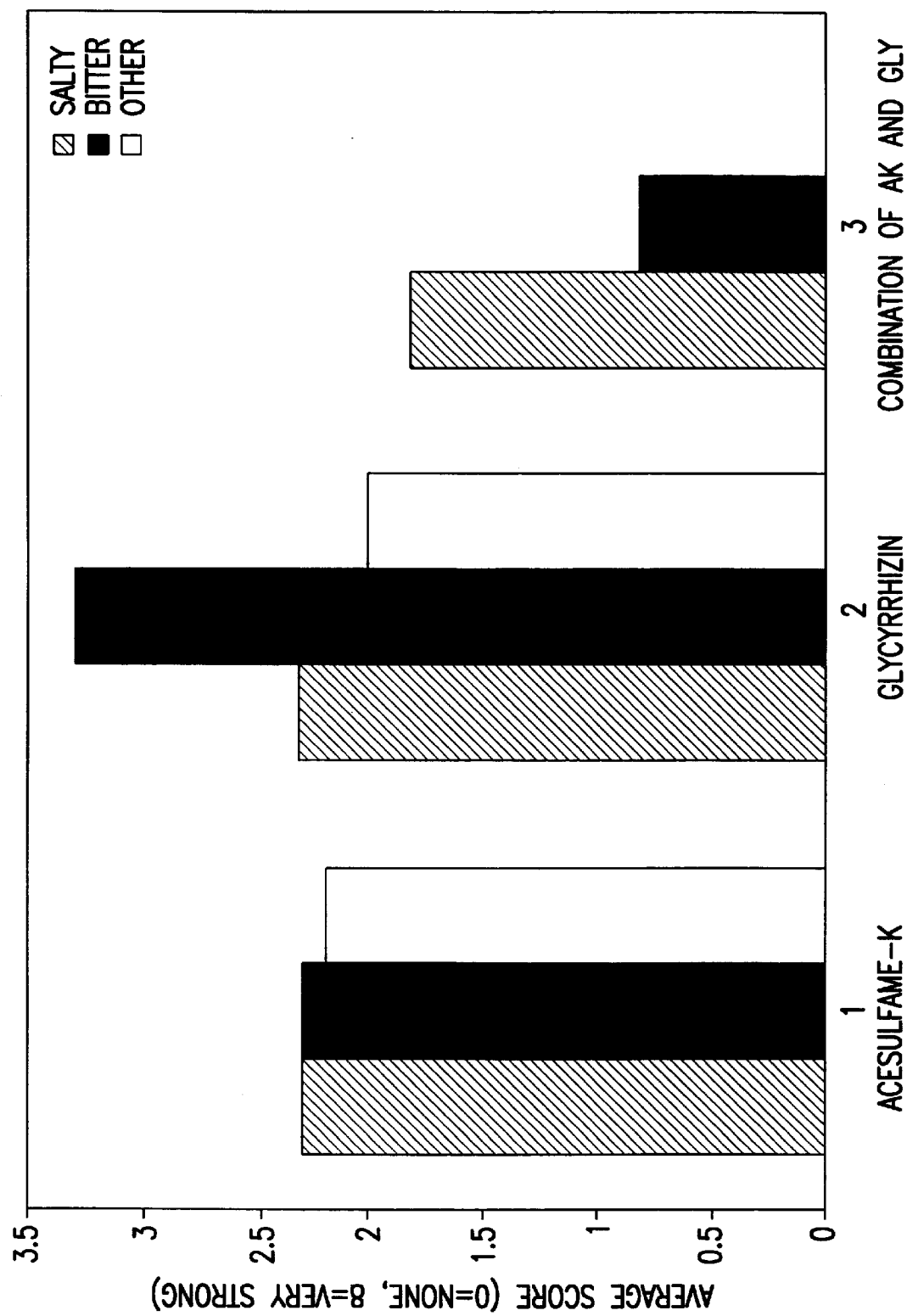
Figure 11:
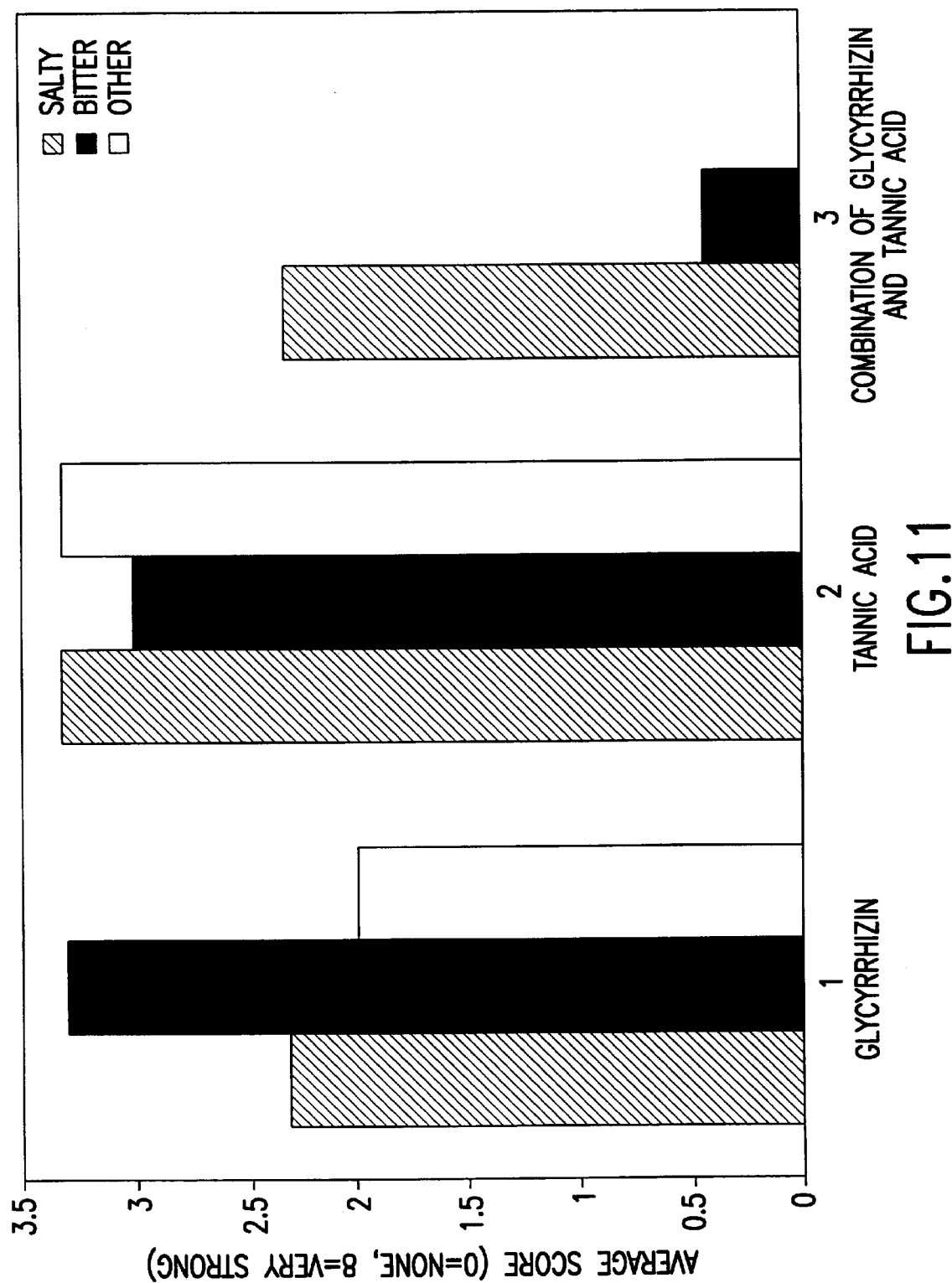
FIG. 11 is a bar graph comparison of the effect of glycyrrhizin, tannic acid and their combination on the taste of KCl solutions.

The present inventors have found that certain agents, when added to ingestible products containing high levels of minerals, result in products with exceptionally good taste compared to the same product without these materials.

By "ingestible product" is meant any food, beverage, nutrition bar, nutritional supplement or pharmaceutical in which it is desirable to minimize a mineral taste.

By "mineral taste" is meant any unpleasant taste associated with a mineral present in an ingestible product, including but not limited to saltiness, bitterness, a metallic taste, or a general "aftertaste."

Beverages containing high levels of minerals, such as potassium, may include sports drinks used to replenish electrolytes, or mineral-enriched beverages designed to be taken with mineral-depleting medications, such as diuretics. While Applicants do not wish to be bound by this theory, it appears that relatively large metal cations are perceived by the nerves associated with taste sensations as bitter, as well as salty. Accordingly, this invention is applicable not only to potassium but other relatively large cations, such as calcium, iron, chromium, copper and zinc.

The materials useful for masking the taste of minerals in accordance with the invention include tannic acid, glycyrrhizin and acesulfame potassium (AK). These materials are effective when added alone, but are more effective when added together, reflecting the presence of a synergistic effect in the masking of mineral tastes.

While not intending to be bound by theory, the mineral taste-reducing materials of the invention appear to function in the following ways. Tannic acid appears to represent a class of compounds which are astringents. Glycyrrhizin is an extract of licorice root. It is distinguished by its sweet aftertaste and licorice menthol aftertaste. It is used extensively to impart sweet flavor to cigars, and is used in Japan to provide sweet and licorice aftertaste to Japanese pickles. Glycyrrhizin appears to act as a flavor modifier and to compete with the mineral on the taste buds. AK is an intense sweetener which is about 200× sweeter than sugar. It is similar in its sweetness potency to aspartame and somewhat less sweet than saccharin.

The tannic acid, glycyrrhizin and acesulfame potassium used in accordance with the present invention, can be used at a concentration of 0.0001–0.5% (W/V) per 1% mineral in the product, more preferably 0.0005–0.25% (W/V) per 1% mineral in the product, and most preferably 0.001–0.05% (W/V) per 1% mineral in the product. The exact amount of mineral taste-masking material to be added to the ingestible product will depend on the concentration and identity of the mineral in the product, and which particular material is used to mask the taste of the mineral, and can be determined by one of skill in the art.

The minerals which are typically found in products to be ingested, and which produce an undesirable taste include, but are not limited to, potassium, magnesium and zinc. The mineral may be present in the ingestible product at a concentration of about 0.25%–10% by weight, preferably 0.5%–5% by weight, and most preferably 1–3% by weight. Other common minerals frequently ingested deliberately in large amounts, for nutritional or medical purposes, or otherwise, include calcium, magnesium, chromium, selenium and copper. In general, any non-toxic, ingestible mineral selected from the alkaline, alkaline earth and transition metals may be addressed with this invention. The present inventors have shown, as described herein below, that the mineral taste associated with products containing these minerals can be masked by the agents of the invention.

Having generally described this invention, a further understanding can be obtained by reference to certain specific examples which are provided herein for purposes of illustration only and are not intended to be limiting unless otherwise specified.

EXAMPLES

Example 1

The effect of tannic acid on potassium-containing beverages was studied. Tannic acid added at levels as low as 5 mg/100 cc of beverage containing 1.26% KCl by weight was effective in reducing and eliminating the aftertaste of KCl.

| Attribute* | Control-no tannic acid added | +5 mg/100 cc tannic acid | +10 mg/100 cc tannic acid | +50 mg/100 cc tannic acid |
|---|---|---|---|---|
| Salt | 2.0 | 1.5 | 1.0 | 1.5 |
| Bitter | 4.5 | 1.0 | 1.0 | 2.5 |
| Aftertaste | 6.0 | 1.0 | 1.0 | 1.0 |

*On a scale of 0 to 8 (0 = none; 8 = extensive)

These data clearly indicate that tannic acid reduces the level of bitter aftertaste without increasing the salty taste. The effective level appears to be between 5 mg/100 ml and 50 mg/100 ml.

Example 2

The effect of glycyrrhizin on potassium-containing beverages was studied. Glycyrrhizin was added at levels of 20–40 mg/100 cc of beverage containing 2.52% KCl by weight was effective in reducing the bitter and metallic aftertaste of KCl.

| Attribute* | Control | +20 mg/100 cc glycyrrhizin | +40 mg/100 cc glycyrrhizin |
|---|---|---|---|
| Salt | 4.0 | 2.5 | 2.0 |
| Bitter | 5.5 | 2.5 | 2.5 |
| Metallic | 6.0 | 2.0 | 2.0 |

*On a scale of 0 to 8 (0 = none; 8 = extensive)

These data clearly indicate that glycyrrhizin is effective in reducing the aftertaste of KCl.

Example 3

AK when added at low levels to solutions containing KCl reduced the perceived bitter aftertaste of these solutions. The level of AK used was 1 to 5 mg/100 ml, which is equivalent in sweetness contribution to between 0.2% and 1% sucrose. This characteristic is specific to AK, and is not noted when AK is substituted for aspartame or saccharin.

Example 4

Additional testing was conducted, comparing the absence of taste modifiers with the three taste modifiers of the invention, both separately, and in combinations (AK and glycyrrhizin) (AK and tannic acid) (glycyrrhizin and tannic acid). These data were evaluated not only for salt and bitterness, but sweet, sour and other taste sensations. In this study, again, 1.26% KCl was prepared, and used as the test medium for all experiments. The aqueous solution was evaluation by an expert panel for each of the taste attributes. The panel consisted of eight individuals who were screened for their taste acuity and trained in the use of the score sheet. The score sheet employed by the panel appears as Table III hereto.

The results of the testing of each test modifier of the invention, individually, are reflected in Table I. Again, as with Examples 1–3, each of the agents was shown to have a significant impact in reducing the bitterness taste, but essentially no impact on sweetness or sourness. The combination of test modifiers, and their impact on the taste of the potassium chloride solution, is reflected in Table II. This table clearly demonstrates the synergistic effect of the combinations presented. Thus, various combinations of the taste modifiers, including two, or all three, can be provided to suppress not only the bitter taste associated, but salts and other flavors as well.

Having now fully described the invention, it will be apparent to one of ordinary skill in the art that many changes and modifications can be made thereto without departing from the spirit or scope of the invention as set forth herein.

TABLE I

AMBI, Inc.
EFFECT OF TASTE MODIFIERS ON TASTE OF KCl SOLUTIONS

|  | Control | Acesulfame-K (mg/100 cc) | | | Glycyrrhizin (mg/100 cc) | | | Tannic Acid (mg/100 cc) | | |
| --- | --- | --- | --- | --- | --- | --- | --- | --- | --- | --- |
|  |  | 2.5 | 5.0 | 7.5 | 5.0 | 10.0 | 20.0 | 1.0 | 5.0 | 10.0 |
| Sweet | 0.0 | 0.0 | 0.0 | 1.3 | 0.0 | 0.0 | 0.5 | 0.0 | 0.0 | 0.0 |
| Sour | 0.0 | 0.0 | 0.0 | 0.0 | 0.0 | 0.0 | 0.0 | 0.0 | 0.0 | 0.0 |
| Salt | 2.5 | 2.8 | 2.3 | 1.5* | 3.5 | 2.3 | 2.0 | 3.3 | 3.8 | 2.0 |
| Bitter | 4.8 | 3.0* | 2.3* | 1.8* | 2.0* | 3.3* | 2.3* | 3.0* | 2.0* | 2.0* |
| Other | 5.5 | 2.8* | 2.2* | 0.5* | 1.0* | 2.0* | 2.0* | 3.3* | 3.0* | 2.0* |

*Indicating statistically significant difference at the 95% confidence level or higher.

TABLE II

AMBI, Inc.
EFFECT OF A COMBINATION OF TASTE MODIFIERS ON TASTE OF KCl SOLUTIONS

| | Acesulfame-K (AK) and Glycynrrhizen (Gly) (mg/100 cc) | | | | Acesulfame-K (AK) and Tannic Acid (TA) (mg/100 cc) | | | |
| --- | --- | --- | --- | --- | --- | --- | --- | --- |
| | 2.5 AK 5 Gly | 2.5 AK 10 Gly | 5 AK 5 Gly | 10 Gly | 2.5 AK 1 TA | 2.5 AK 5 TA | 5 AK 1 TA | 5 AK 5 TA |
| Sweet | 0.0 | 0.0 | 1.0 | 1.0 | 0.0 | 0.0 | 0.0 | 0.0 |
| Sour | 0.0 | 0.0 | 0.0 | 0.0 | 0.0 | 0.0 | 0.0 | 0.0 |
| Salt | 3.0 | 1.9 | 1.4 | 1.8 | 2.3 | 2.3 | 1.3 | 0.8 |
| Bitter | 2.3 | 1.5 | 0.3 | 0.8 | 0.5 | 0.5 | 0.0 | 0.0 |
| Other | 3.0 | 0.8 | 0.5 | 0.0 | 0.8 | 0.5 | 0.5 | 0.0 |

| | Glycyrrhizinn (Gly) and Tannic Acid (TA) (mg/100 cc) | | | |
| --- | --- | --- | --- | --- |
| | 5 Gly 1 TA | 5 Gly 5 TA | 5 Gly 1 TA | 5 Gly 5 TA |
| Sweet | 0.0 | 0.0 | 0.0 | 0.0 |
| Sour | 0.0 | 0.0 | 0.0 | 0.0 |
| Salt | 2.0 | 2.9 | 2.3 | 2.3 |
| Bitter | 0.4 | 0.8 | 0.4 | 0.4 |
| Other | 0.0 | 0.0 | 0.0 | 0.0 |

TABLE III

AMBI, Inc.
AMBI -- KCl (1.26% SOLUTION SCORE SHEET

Sweet

| 0 | 1 | 2 | 3 | 4 | 5 | 6 | 7 | 8 |
|---|---|---|---|---|---|---|---|---|
| None | | Slight | | Definite | | Strong | | Extensive |

Sour

| 0 | 1 | 2 | 3 | 4 | 5 | 6 | 7 | 8 |
|---|---|---|---|---|---|---|---|---|
| None | | Slight | | Definite | | Strong | | Extensive |

Salt

| 0 | 1 | 2 | 3 | 4 | 5 | 6 | 7 | 8 |
|---|---|---|---|---|---|---|---|---|
| None | | Slight | | Definite | | Strong | | Extensive |

Bitter

| 0 | 1 | 2 | 3 | 4 | 5 | 6 | 7 | 8 |
|---|---|---|---|---|---|---|---|---|
| None | | Slight | | Definite | | Strong | | Extensive |

Other

| 0 | 1 | 2 | 3 | 4 | 5 | 6 | 7 | 8 |
|---|---|---|---|---|---|---|---|---|
| None | | Slight | | Definite | | Strong | | Extensive |

Describe: _____

What is claimed is:

1. A method for reducing unpleasant taste or aftertaste caused by the presence of a mineral in an ingestible product, comprising adding to said ingestible product an amount of a flavor masking agent selected from the group consisting of tannic acid, glycyrrhizin, acesulfame potassium and two or more thereof sufficient to reduce the unpleasant taste or aftertaste caused by the mineral, wherein the mineral is selected from the group consisting of potassium, calcium, magnesium, iron, chromium, copper, zinc, and two or more of the minerals, and wherein the amount of the flavor masking agent added to the ingestible product is 0.001–0.05% (W/V) per 1% mineral (W/V).

2. The method of claim 1, wherein tannic acid is added to the ingestible product.

3. The method of claim 2, wherein the amount of tannic acid added to the ingestible product is at least 0.004% (W/V) per 1% mineral (W/V).

4. The method of claim 1, wherein the flavor masking agent is glycyrrhizin.

5. The method of claim 4, wherein the amount of glycyrrhizin added to the ingestible product is at least 0.008% (W/V) per 1% mineral (W/V).

6. A composition comprising at least one element which causes an unpleasant taste or aftertaste upon oral ingesting, said element consisting essentially of a mineral which produces the unpleasant taste or aftertaste, and an amount of a flavor masking agent sufficient to reduce the unpleasant taste or aftertaste caused by the mineral, wherein the mineral is selected from the group consisting of potassium, calcium, magnesium, iron, chromium, copper, zinc, and two or more of the minerals and the flavor masking agent is selected from the group consisting of tannic acid, glycyrrhizin, acesulfame potassium and two or more thereof, and wherein the flavor masking agent comprises tannic acid.

7. The composition of claim 6, wherein the amount of tannic acid in the composition is at least 0.004% (W/V) per 1% mineral (W/V).

8. A composition comprising at least one element which causes an unpleasant taste or aftertaste upon oral ingesting, said element consisting essentially of a mineral that produces the unpleasant taste or aftertaste, and an amount of a flavor masking agent sufficient to reduce the unpleasant taste or aftertaste caused by the mineral, wherein the mineral is selected from the group consisting of potassium, calcium, magnesium, iron, chromium, copper, zinc, and two or more of the minerals and the flavor masking agent is selected from the group consisting of tannic acid, glycyrhizin, acesulfame potassium and two or more thereof, and wherein the flavor masking agent is glycyrrhizin.

9. The composition of claim 8, wherein the amount of glycyrrhizin in the composition is at least 0.008% (W/V) per 1% mineral (W/V).

10. A composition comprising at least one element which causes an unpleasant taste or aftertaste upon oral ingesting, said element consisting essentially of a mineral that produces the unpleasant taste or aftertaste, and an amount of a flavor masking agent sufficient to reduce the unpleasant taste or aftertaste caused by the mineral, wherein the mineral is selected from the group consisting of potassium, calcium, magnesium, iron, chromium, copper, zinc, and two or more of the minerals and the flavor masking agent is selected from the group consisting of tannic acid, glycyrrhizin, acesulfame potassium and two or more thereof, and wherein the flavor masking agent is acesulfame potassium.

11. The composition of claim 10, wherein the amount of acesulfame potassium in the composition is at least 0.001% (W/V) per 1% mineral (W/V).

12. A composition comprising at least one element which causes an unpleasant taste or aftertaste upon oral ingesting, said element consisting essentially of a mineral that produces the unpleasant taste or aftertaste, and an amount of a flavor masking agent sufficient to reduce the unpleasant taste or aftertaste caused by the mineral, wherein the mineral is selected from the group consisting of potassium, calcium, magnesium, iron, chromium, copper, zinc, and two or more of the minerals and the flavor masking agent is two or more agents selected from the group consisting of tannic acid, glycyrrhizin and acesulfame potassium.

* * * * *